(12) United States Patent
Grafman et al.

(10) Patent No.: US 10,753,949 B2
(45) Date of Patent: Aug. 25, 2020

(54) BIOMARKERS IN NASAL EXHALED BREATH

(71) Applicants: REHABILITATION INSTITUTE OF CHICAGO, Chicago, IL (US); NORTHWESTERN UNIVERSITY, Evanston, IL (US)

(72) Inventors: Jordan Grafman, Riverwoods, IL (US); Christina M. Zelano, Chicago, IL (US); Katherina K. Hauner, Chicago, IL (US)

(73) Assignees: REHABILITATION INSTITUTE OF CHICAGO, Chicago, IL (US); NORTHWESTERN UNIVERSITY, Evanston, IL (US)

( * ) Notice: Subject to any disclaimer, the term of this patent is extended or adjusted under 35 U.S.C. 154(b) by 582 days.

(21) Appl. No.: 15/452,074

(22) Filed: Mar. 7, 2017

(65) Prior Publication Data
US 2017/0254817 A1    Sep. 7, 2017

Related U.S. Application Data

(60) Provisional application No. 62/304,887, filed on Mar. 7, 2016.

(51) Int. Cl.
*G01N 33/68* (2006.01)
*A61B 10/00* (2006.01)
(Continued)

(52) U.S. Cl.
CPC ......... *G01N 33/6896* (2013.01); *A61B 5/082* (2013.01); *A61B 5/4088* (2013.01); *A61B 10/00* (2013.01); *G01N 33/497* (2013.01);
*A61B 5/097* (2013.01); *A61B 2010/0087* (2013.01); *G01N 2333/4709* (2013.01);
(Continued)

(58) Field of Classification Search
CPC .. G01N 33/6896; G01N 33/497; A61B 5/082; A61B 5/083; A61B 5/091; A61B 5/4088; A61B 5/097; A61B 2010/0087
See application file for complete search history.

(56) References Cited

U.S. PATENT DOCUMENTS 5,046,491 A * 9/1991 Derrick ............... A61B 5/097
128/200.24
8,945,935 B2 2/2015 Haick et al.
(Continued)

OTHER PUBLICATIONS

Bach et al. 'Measuring Compounds in Exhaled Air to Detect Alzheimer's Disease and Parkinson's Disease'; PLoS ONE; DOI: 10.1371/journal.pone.0132227; Jul. 13, 2015; pp. 1/13-13/13 (Year: 2015).*

(Continued)

*Primary Examiner* — Patrick Fernandes
(74) *Attorney, Agent, or Firm* — Faegre Drinker Biddle & Reath LLP

(57) ABSTRACT

A method of diagnosing or assessing risk of a tauopathy in a person is disclosed. The method may comprise collecting a nasal sample of exhaled breath from the person's nose, analyzing the nasal sample to detect the presence of tau protein in the sample, and determining the concentration of tau protein in the nasal sample, wherein the tau protein concentration in the nasal sample indicates susceptibility to the tauopathy.

11 Claims, 7 Drawing Sheets

(51) Int. Cl.
- *G01N 33/497* (2006.01)
- *A61B 5/08* (2006.01)
- *A61B 5/00* (2006.01)
- *A61B 5/097* (2006.01)

(52) U.S. Cl.
CPC .............. *G01N 2800/2814* (2013.01); *G01N 2800/2821* (2013.01); *G01N 2800/50* (2013.01)

(56) References Cited

U.S. PATENT DOCUMENTS

| | | |
|---|---|---|
| 2009/0163825 A1 | 6/2009 | Hirsh et al. |
| 2014/0294839 A1 | 10/2014 | Kuret et al. |

OTHER PUBLICATIONS

Mika Shirasu, Kazushige Touhara, The scent of disease: volatile organic compounds of the human body related to disease and disorder, The Journal of Biochemistry, vol. 150, Issue 3, Sep. 2011, pp. 257-266, https://doi.org/10.1093/jb/mvr090 (Year: 2011).*

PCT Search Report and Written Opinion issued in related application PCT/US2017/021127, dated Jun. 6, 2017, 11 pages.

Baker et al., "Magnetic bones in human sinuses," Nature, Jan. 1983, Nature Publishing Group, vol. 301, pp. 78-80.

Bedussi et al., "Clearance from the mouse brain by convection of interstitial fluid towards the ventricular system," Fluids Barriers CNS, 2015, 12:23, 13 pages.

Eide et al., "MRI with intrathecal MRI gadolinium contrast medium administration: a possible method to assess glymphatic function in human brain," Acta Radiologica Open, 2015, vol. 4(11), pp. 1-5.

Ethell, "Disruption of Cerebrospinal Fluid Flow through the Olfactory System May Contribute to Alzheimer's Disease Pathogenesis," Journal of Alzheimer's Disease, 2014, IOS Press, vol. 41, pp. 1021-1030.

Hui, "Clearing Your Mind: A Glymphatic System?" World Neurosurgery, May 2015, vol. 83(5), pp. 715-717.

Hyman et al., "Pathologic Changes in the Olfactory System in Aging and Alzheimer's Disease," Annals of the New York Academy of Sciences, 1991, pp. 14-19.

Massler, "Geriatric nutrition: The role of taste and smell in appetite," The Journal of Prosthetic Dentistry, Mar. 1980, vol. 43(3), pp. 247-250, Abstract, 2 pages.

Perls et al., "Higher Respiratory Infection Rates on an Alzheimer's Special Care Unit and Successful Intervention," Journal of the American Geriatric Society, 1995, vol. 43(12), pp. 1341-1344.

Weller et al., "Pathology of Cerebrospinal Fluid and Interstitial Fluid of the CNS: Significance for Alzheimer Disease, Prion Disorders and Multiple Sclerosis," Journal of Neuropathology and Experimental Neurology, Oct. 1998, vol. 57(10), pp. 885-894.

Yang et al., "Evaluating glymphatic pathway function utilizing clinically relevant intrathecal infusion of CSF tracer," Journal of Translational Medicine, 2013, 11:107, pp. 1-9.

Huttmann et al., "Comparison of Two Devices and Two Breathing Patterns for Exhaled Breath Condensate Sampling," PLoS ONE, Nov. 2011, vol. 6 (11), e27467, pp. 1-10.

* cited by examiner

BIOMARKERS IN NASAL EXHALED BREATH

CROSS-REFERENCE TO RELATED APPLICATIONS

The present application claims the priority benefit of U.S. Provisional Patent Application 62/304,887, filed on Mar. 7, 2016 and incorporated herein by reference.

BACKGROUND

Certain diseases and conditions cause a change in the concentration of certain molecules in the human brain. For example, in Alzheimer's disease there is an increase in the concentration of molecules such as the tau protein. The blood-brain barrier is thought to block the passage of certain molecules, so that they do not pass into the bloodstream. This has limited the ability of clinicians to use blood samples from a patient in order to diagnose the patient as having brain-related diseases such as Alzheimer's disease.

It would be of great benefit for patients and the medical community to have systems, devices, and methods that allow for the assessment of the brain's condition or for the diagnosis of conditions that affect the human brain, based on exhaled breath through the human nose. Breath detection is currently performed through the analysis of mouth breath, rather than nasal breath, with the goal of measuring compounds that are present in the lungs and may indicate diseases that affect the respiratory airways.

BRIEF SUMMARY

In various embodiments, a method is disclosed that involves collecting a sample of exhaled breath from a patient's nose and analyzing the sample with an assay to detect a concentration of at least one biomarker. The method may further include correlating the biomarker concentration with at least one medical condition. The method may further include collecting a sample of exhaled breath from a patient's mouth; analyzing the mouth sample with an assay to detect a concentration of at least one biomarker; and subtracting the mouth concentration from the nose concentration to determine an adjusted biomarker concentration. The method may further comprise correlating the adjusted biomarker concentration with at least one medical condition.

In various embodiments, the method may comprise collecting a sample of exhaled breath from a person's nose and analyzing the sample to detect the presence of at least one biomarker. The method may further comprise measuring the concentration of the neural biomarker. The method may further comprise correlating the neural biomarker concentration with at least one medical condition. The method may further comprise collecting a sample of exhaled breath from a patient's mouth, analyzing the mouth sample with an assay to detect a concentration of at least one biomarker, and subtracting the mouth concentration from the nose concentration to determine an adjusted biomarker concentration. The method may further comprise correlating the adjusted biomarker concentration with at least one medical condition.

In various embodiments, a method of determining the presence of a biomarker in the brain of a person, comprising determining the presence of the biomarker in the exhaled nasal breath of the person. The method may comprise assessing the condition of the person's brain.

In various embodiments, a method for assessing the condition of a person's brain may comprise determining the presence of one or more biomarkers in the exhaled nasal breath of the person. The neural biomarker's presence may be determined in a condensed sample of exhaled nasal breath. The neural biomarker's presence may be determined in a vapor sample of exhaled nasal breath. A concentration of the biomarker may be determined.

In various embodiments, a method may comprise analyzing a sample of exhaled nasal breath from a person to determine the presence of one or more neural biomarkers in the nasal breath. In various embodiments, a method for analyzing the chemical state of a person's brain may comprise determining the composition of the person's exhaled nasal breath. The composition of the person's nasal breath may be determined using a condensed sample of exhaled nasal breath. In various embodiments, a method for assessing the condition of a person's brain may comprise determining the tau concentration in a sample of exhaled nasal breath. The methods may further comprise correlating the tau concentration with at least one medical condition. The tau concentration may be determined from a condensed sample of exhaled nasal breath. The tau concentration may be determined from a vapor sample of exhaled nasal breath. The medical condition may be Alzheimer's disease or dementia.

In various embodiments, a method of diagnosing or assessing risk of a tauopathy in a person may comprise collecting a nasal sample of exhaled breath from the person's nose; analyzing the nasal sample to detect the presence of tau protein in the sample; and determining the concentration of tau protein in the nasal sample, wherein the tau protein concentration in the nasal sample indicates susceptibility to the tauopathy. The method may further comprise collecting a mouth sample of exhaled breath from the patient's mouth; analyzing the mouth sample to detect the presence of tau protein and the concentration of tau protein in the mouth sample; and determining the difference between the concentration of tau protein in the nasal sample and the concentration of tau protein in the mouth sample, wherein the difference indicates susceptibility to Alzheimer's disease or dementia. The tauopathy may be Alzheimer's disease or may be dementia, among other tauopathies.

DETAILED DESCRIPTION

The noninvasive nature of exhaled nasal breath collection renders the methods of this disclosure particularly attractive as diagnostic tools, especially for patients who may otherwise need to undergo more invasive laboratory testing to diagnose conditions or illnesses of neural origin, such as tauopathies. One tauopathy is Alzheimer's disease (AD).

Figure 1:
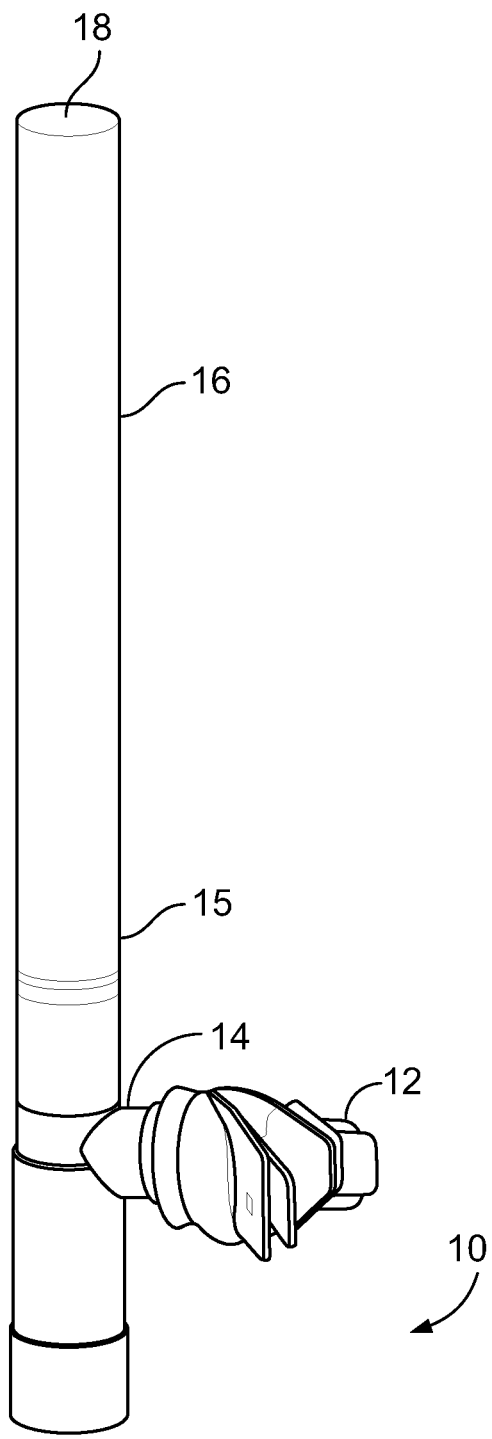
FIG. 1 is a perspective view of an embodiment of a nasal breath collection device.

Systems and methods are disclosed that relate to testing for detection of biomarkers of neurological conditions via nasally exhaled breath. The testing may be compared to orally exhaled breath. FIG. 1 shows a perspective view of an embodiment of a nasal breath collection device 10. A patient exhales through the nose into the nasal mask 12. The exhaled air passes through a first valve 14 and a second valve 15, and condenses on the surface of the tube 16. The first valve 14 is preferably a one-way valve that allows the patient to breath in and out through the breath collection device 10. The second valve 15 may be positioned higher in the tube and allow air to go into the tube but not back down into the inlet. The first valve 14 may be made of silicone rubber or another appropriate material. Before the patient's breath is collected in the tube 16, a cooling sleeve (not shown) is slid over the tube 14 to cause the breath to condensate into the tube 14 while the patient breaths normally into the inlet. Following breath collection, an end cap (not shown) may be placed over the top opening 18 so that air and condensate do not escape from the tube. The end cap may be made from a medically appropriate vinyl or other appropriate material. The cooling sleeve is kept at a cold temperature until being used, for instance by being stored in a freezer. The cooling sleeve may be made from aluminum or another appropriate cooling material. Once the breath has condensed in the tube 16, a plunger may be used to extract droplets stuck to the inside wall of the tube 16. In an embodiment, the valve 14 may be used as a plunger to extract the droplets.

In another embodiment, to collect the exhaled breath vapor, a patient may fill a tedlar bag fitted with a teflon check valve at the inlet, allowing patients to breathe continuously with the bag attached. Using a tedlar bag also allows for the collection of breath vapor, which allows for analysis for detection of smaller molecules, such as nitrous oxide, that may not be collected in breath condensate. Tedlar bags like the 1-L Tedlar® bag with connected Teflon tube (Sigma-Aldrich, St. Louis, Mo.) may be used.

Figure 2:
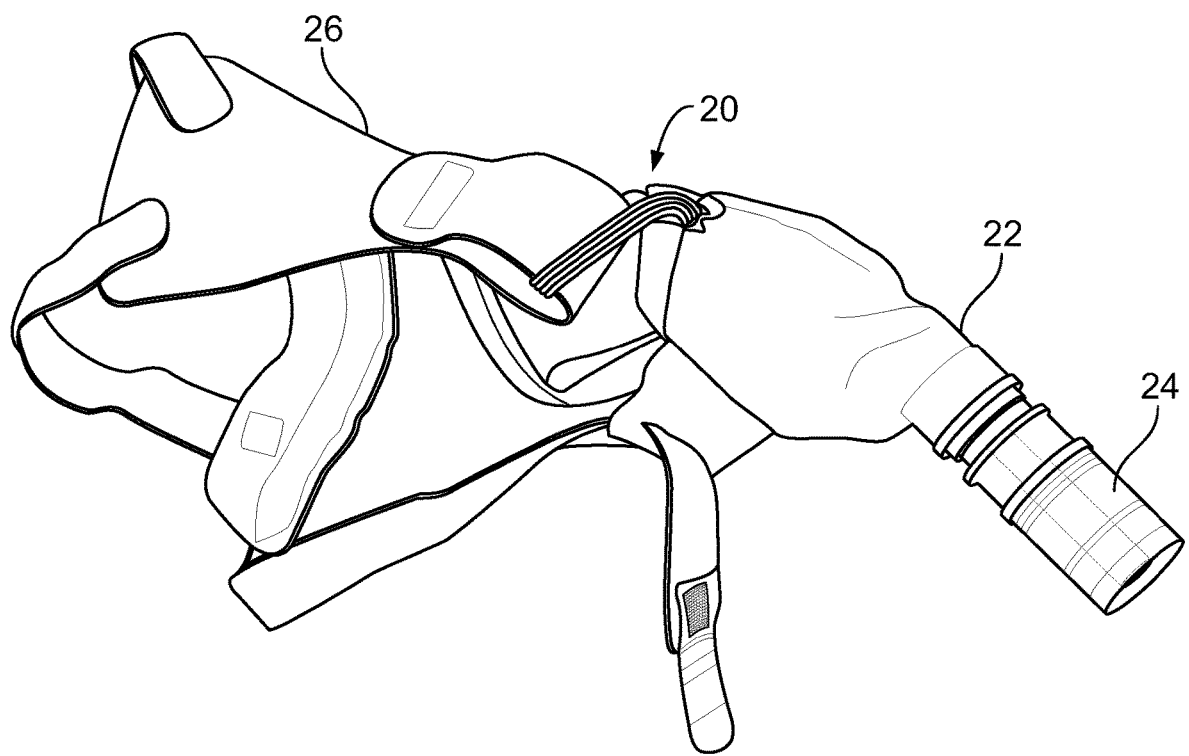
FIG. 2 is a perspective view of another embodiment of a nasal breath collection device.

FIG. 2 shows another embodiment of a nasal breath collection device 20. The patient wears a mask 22 over his or her nose, and breaths out of the nostrils and into a tube 24, which is connected to a condensate system. The patient may use head strap 26 to keep the mask 22 in place.

In an embodiment, a patient may be asked to complete one or more tasks before their breath is collected. This allows a clinician to analyze breath before the task with breath after the task, therefore providing additional brain-state information. For instance, a patient may be asked to perform one or more stress tasks, such as public speaking, mental arithmetic, placing their hands in cold water, or very mild electrical stimulation. As another example, a patient may be shown one or words on a computer screen, and asked to imagine familiar odors associated with the shown words. Words will be shown that are associated with pleasant or neutral scents (such as "lemon", "mint", "pine", or "rose") as well as words associated with unpleasant scents (such as "rotten eggs" or "fish"). This task is meant to induce a sensory response in the olfactory cortical and bulbar brain areas, which are close in proximity to the olfactory mucosa and the nose. In other embodiments, the patient may be administered medicine or an external stimulus, such as caffeine or nicotine, that alters the flow of tissues in the nasal passage. Doing so may cause an adjustment in the concentration of biomarkers that are found in nasally exhaled breath.

Collecting breath. In an embodiment, breath condensate and/or breath volatiles may be collected from the nose and/or mouth of, preferably, naturally breathing, healthy and/or compromised human participants. This allows for the identification of particular molecules of interest that are specific to nasally exhaled breath in comparison to orally exhaled breath. In the basic embodiment, only nasal breath is collected.

The terms, neural substance, neural compound, neural molecule, neural biomarker, all refer to species which are located in or are directly associated with the brain whether a normal or compromised brain, reflecting disease or abnormality. These include all species in the cerebral spinal fluid. Generally, these will be proteins, peptides, small acids, nucleic acids and fragments (e.g., DNA, RNA, etc), neurotransmitters, etc. Methods for assaying such species are already well known and include, for example, immunological and nucleic acid based techniques. These methodologies are readily adaptable to any new entities, such as by routine generation of corresponding new antibodies or fragments, routine nucleic acid sequencing and preparation, etc.

Such biomarkers could include, for example, various plasma proteins, neopterin, potassium, chloride, glucose, and albumin. Specifically in condensed breath samples, they may include isoprostanes, prostaglandins, leukotrines, nitrites and nitrates, hydrogen peroxide, or cytokines. In volatile breath, any of the following compound biomarkers may be identified: ethane, pentane, hexanal, octanal, nonanal, propanal, butanol, hydrocarbons, or ketones.

Certain stress-related biomarkers may be found in exhaled nasal breath, which may include cytokines (in particular IL-1 and IL-6), T lymphocytes, TNF-alpha, Chromogranin-A, alpha amylase, cortisol, adrenocorticotropic hormone, dopamine, norepinephrine, and epinephrine.

In another embodiment, biomarker compounds may be specifically targeted which have a known link with Alzheimer's disease (AD) symptoms, including beta amyloid (Aβ40, Aβ42), tau (T-tau, phosphorylated tau-181), and α-synuclein. Tau protein abnormalities are key pathogenic features of Alzheimer disease and other neurodegenerative diseases. Tau protein abnormalities also may be found in other tauopathies, such as progressive supranuclear palsy, chronic traumatic encephalopathy and frontotemporal lobar degeneration. Tauopathies are diseases in which insoluble deposits of tau protein aggregate in neurons and/or glia. Tau-dependent cytotoxic mechanisms are often found in neurodegenerative disorders, occurring not only in AD, but also in conditions such as chronic (CTE) and parkinsonian disorders. These mechanisms can involve post-translational modifications of tau, including hyperphosphorylation, cleavage and aggregation.

Other biomarkers may include 5-hydroxyindolacetic acid and beta-2-transferrin.

Other protein biomarkers may include:

Axonal Proteins:

α II spectrin (and SPDB)—1; NF-68 (NF-L)—2; Tau—3; β II, III spectrin; NF-200 (NF-H); NF-160 (NF-M); Amyloid precursor protein; α internexin.

Dendritic Proteins:

betaIII-tubulin—1; p24 microtubule-associated protein—2; alpha-Tubulin (P02551); beta-Tubulin (P04691); MAP-2A/B—3; MAP-2C—3; Stathmin—4 Dynamin-1 (P21575); Phocein; Dynactin (Q13561); Vimentin (P31000); Dynamin; Profilin; Cofilin 1,2; Somal Proteins; UCH-L1

(Q00981)—1; Gyocogen phosphorylase-BB—2; PEBP (P31044); NSE (P07323); CK-BB (P07335); Thy 1.1; Prion protein; Huntingtin; 14-3-3 proteins (e.g. 14-3-3-epsolon (P42655)); SM22-α; Calgranulin AB; alpha-Synuclein (P37377); beta Synuclein (Q63754); HNP 22.

Neural Nuclear Proteins.

NeuN—1; S/G(2) nuclear autoantigen (SG2NA); Huntingtin.

Presynaptic Proteins:

Synaptophysin—1; Synaptotagmin (P21707); Synaptojanin-1 (Q62910); Synaptojanin-2; Synapsin1 (Synapsin-Ia); Synapsin2 (Q63537); Synapsin3; GAP43; Bassoon (NP_003449); Piccolo (aczonin) (NP_149015); Syntaxin; CRMP1, 2; Amphiphysin—1 (NP_001626); Amphiphysin—2 (NP_647477).

Post-Synaptic Proteins.

PSD95—1; NMDA-receptor (and all subtypes)—2; PSD93; AMPA-kainate receptor (all subtypes); mGluR (all subtypes); Calmodulin dependent protein kinase II (CAMPK)-alpha, beta, gamma; CaMPK-IV; SNAP-25; a-/b-SNAP.

Other nervous cell subtype biomarkers may include:

Myelin-Oligodendrocyte.

Myelin basic protein (MBP) and fragments; Myelin proteolipid protein (PLP); Myelin Oligodendrocyte specific protein (MOSP); Myelin Oligodendrocyte glycoprotein (MOG); myelin associated protein (MAG); Oligodendrocyte NS-1 protein.

Glial Protein Biomarkers.

GFAP (P47819); Protein disulfide isomerase (PDI)— P04785; Neurocalcin delta; S100beta.

Microglia Protein Biomarkers:

Ibal; OX-42; OX-8; OX-6; ED-1; PTPase (CD45); CD40; CD68; CD11b; Fractalkine (CX3CL1) and Fractalkine receptor (CX3CR1); 5-d-4 antigen.

Schwann Cell Markers.

Schwann cell myelin protein.

Glia Scar.

Tenascin.

Other anatomical brain biomarkers (CNS+PNS) may include:

Anatomical brain biomarkers (CNS+PNS) may include:

Hippocampus.

Stathmin, Hippocalcin, SCG10.

Cerebellum:

Purkinje cell protein-2 (Pcp2), Calbindin D9K, Calbindin D28K (NP_114190), Cerebellar CaBP, spot 35.

Cerebrocortex:

Cortexin-1 P60606, H-2Z1 gene product

Thalamus.

CD15 (3-fucosyl-N-acetyl-lactosamine) epitope.

Hypothalamus.

Orexin receptors (OX-1R and OX-2R)-appetite, Orexins (hypothalamus-specific peptides).

Corpus Callosum.

MBP, MOG, PLP, MAG.

Spinal Cord.

Schwann cell myelin protein.

Striatum.

Striatin; Rhes (Ras homolog enriched in striatum).

Peripheral Ganglia.

Gadd45a.

Peripherial Nerve Fiber(Sensory+Motor).

Peripherin; Peripheral myelin protein 22 (AAH91499).

Other Neuron-Specific Proteins.

PH8 (S Serotonergic Dopaminergic); PEP-19 (a neuron-specific protein); Neurocalcin (NC), a neuron-specific EF-hand Ca2+-binding protein; Encephalopsin; Striatin; SG2NA; Zinedin; Recoverin; Visinin.

Other neurotransmitter receptor biomarkers may include: NMDA receptor subunits (e.g. NR1A2B); Glutamate receptor subunits (AMPA, Kainate receptors (e.g. GluR1, GluR4); beta-adrenoceptor subtypes (e.g. beta(2)); Alpha-adrenoceptors subtypes (e.g. alpha(2c)); GABA receptors (e.g. GABA(B)); Metabotropic glutamate receptor (e.g. mGluR3); 5-HT serotonin receptors (e.g. 5-HT(3)); Dopamine receptors (e.g. D4); Muscarinic Ach receptors (e.g. M1); Nicotinic Acetylcholine Receptor (e.g. alpha-7).

Other neurotransmitter transporter biomarkers may include: Norepinephrine Transporter (NET); Dopamine transporter (DAT); Serotonin transporter (SERT); Vesicular transporter proteins (VMAT1 and VMAT2); GABA transporter vesicular inhibitory amino acid transporter; (VIAAT/VGAT); Glutamate Transporter (e.g. GLT1); Vesicular acetylcholine transporter; Vesicular Glutamate Transporter 1 [VGLUT1; BNPI] and VGLUT2 Choline transporter, (e.g. CHT1).

Other biomarkers of neuron subtypes based on a neurotransmitter system may include:

Cholinergic Biomarkers:

Acetylcholine Esterase; Choline acetyltransferase [ChAT].

Dopaminergic Biomarkers:

Tyrosine Hydroxylase (TH); Phospho-TH; DARPP32; Noradrenergic Biomarkers; Dopamine beta-hydroxylase (DbH).

Adrenergic Biomarkers:

Phenylethanolamine N-methyltransferase (PNMT); Serotonergic Biomarkers; Tryptophan Hydroxylase (TrH).

Glutamatergic Biomarkers.

Glutaminase; Glutamine synthetase.

GABAergic Biomarkers.

GABA transaminase [GABAT]); GABA-B-R2. Nasally exhaled breath may be collected in any conventional fashion; for instance, during a single 10- to 20-minute collection procedure or in regular intervals. Samples may be stored for later analysis. Collection may be improved when patients receive instruction on how to make regular, consistent inhalations and exhalations through the nose, and be given an opportunity to practice this procedure. Patients may perform tidal breathing through the nose. In a preferred embodiment, the patient's breathing rate should be monitored carefully to ensure the patient maintains a steady respiratory pattern, which is preferred. In an embodiment, the patient's respiration may be monitored with a real-time trace using a pressure transducer. The pressure transducer may be attached to the nasal mask. This allows for both real-time monitoring of patient breathing and also offline analysis.

Breath collection can take place in a room with purified air, and subjects sit in this room breathing normally for a period of time prior to the initiation of the breath collection procedure. The patient may sit in the room with purified air for various periods of time. The time can be at least 4 minutes as the lung can be washed out in approximately 4 minutes if a patient breathes pure air. Additionally, an ambient air sample may be collected concurrently with each collected breath sample. This ambient air sample may be analyzed in the same way as the breath sample.

Breath may be collected separately from each nostril of the nose. Biomarkers found in breath from one nostril may be compared to biomarkers found in breath from the other nostril. Any lateralized differences in biomarker concentrations in the brain may be reflected in single nostril breath.

The comparison of biomarkers in separate nostril breaths may be used to diagnose certain conditions, for example, conditions that affect one hemisphere of the brain. Analysis. Patients with certain conditions have differentiated levels of certain biomarkers and their related compounds. For example, patients with Alzheimer's disease, Frontotemporal Dementia, or traumatic brain injury (TBI) have differentiated levels of tau compared to individuals without these conditions. Similarly, patients with stress have differentiated levels of cytokines; and individuals who experience greater social inclusiveness have differentiated levels of oxytocin or vasopressin; and patients with differentiated levels of brain-derived neurotrophic factor (BNDF) experience greater plasticity. Likewise, mood is affected by insulin-like growth factor (IGF) and cortical function is affected by vascular endothelial growth factor (VEGF). Nasal breath samples may be analyzed for one or more biomarkers to indicate the likelihood that a patient has a medical condition. The analysis may detect the presence or absence of one or more biomarkers. The analysis may detect the concentration of one or more biomarkers. The analysis may compare its results with that of another sample, such as a mouth breath sample, to determine an adjusted biomarker concentration.

Breath samples may be analyzed using Gas-Chromatographic techniques combined with Mass Spectrometry. The resultant spread of molecular peaks may be analyzed using statistical software, such as Matlab software (Mathworks).

Raw binary files that are outputted by the statistical software may be converted to ASCII files containing the measured intensities for all channel indices of the spectra. A peak detection algorithm may be used to yield a list of peak positions for each individual spectrum, which may be used to create a matrix displaying the frequency of each peak position for each sample. Following normalization, peaks from the nasal and orally obtained breath may be subtracted to identify peaks that differ across the mouth and nose. Mass spectroscopy may be used to identify the chemical composition of the peaks. In some embodiments, a breath sample may be analyzed using a very sensitive ELISA assay, such as the Simoa™ (Single Molecule Array) array (Quanterix, Lexington, Mass.). Such a system makes use of arrays of femtoliter-sized reaction chambers, termed single-molecule Arrays, that can isolate and detect single enzyme molecules. Because the array volumes are approximately 2 billion times smaller than a conventional ELISA, a rapid buildup of fluorescent product is generated if a protein labeled with GFP, YFP, BFP or any other fluorescent marker is present. With diffusion defeated, this high local concentration of product can be readily observed. For certain such systems, only one single molecule is needed to reach the detection limit. One such system is described further in U.S. Patent Publication No. 2015/0141272 to Neil Gordon, titled "Ultrasensitive detection of extremely low level biological analytes using electrochemical signal amplification and biosensor", filed Feb. 5, 2014 and incorporated herein by reference in its entirety.

In other embodiments, a method of diagnosing or assessing risk of Alzheimer's disease or dementia in a person may be employed. The method may comprise collecting a nasal sample of exhaled breath from the person's nose; analyzing the nasal sample to detect the presence of tau protein in the sample; and determining the concentration of tau protein in the nasal sample, wherein the tau protein concentration in the nasal sample indicates susceptibility to Alzheimer's disease or dementia. The method may further comprise collecting a mouth sample of exhaled breath from the patient's mouth; analyzing the mouth sample to detect the presence of tau protein and the concentration of tau protein in the mouth sample; and determining the difference between the concentration of tau protein in the nasal sample and the concentration of tau protein in the mouth sample, wherein the difference indicates susceptibility to Alzheimer's disease or dementia.

Nasal and oral breath condensate samples can be measured for tau concentration. Ways of measuring tau concentration include an HD-1 analysis, such as the Simoa HD-1 Analyzer (Quanterix, Lexington, Mass.

Various tests can be used to assess the extent of Alzheimer's and dementia in a patient. These tests can ask patients and/or their caregivers about their habits and can include questions that directly test memory and other brain functions. Two exemplary tests are the Activities of Daily Living Questionnaire (ADLQ) and the Trail Making Test. The higher the ADLQ score (completed by caregiver), the more dysfunctional the study subject is. Similarly, a higher Trail Making test score reflects a longer amount of time required to complete the test, indicating a higher dysfunction of the study subject.

In a study, sets of nasal and oral breath condensate samples were measured for total Tau concentration with validated assays utilizing the Simoa HD-1 Analyzer (Quanterix, Lexington, Mass.). The Simoa™ Tau kit (Product #: 101444) was used. The study subjects provided a nasal breath sample and an oral breath sample. The study subjects were tested with two tests. The first test was the Activities of Daily Living Questionnaire (ADLQ), an information-based assessment of functional abilities used to assess patients with probable Alzheimer disease. The ADLQ can measure functioning in the areas of self-care, household care, employment and recreation, shopping and money, travel, and communication. The second test was the Trail Making Test, a neuropsychological test that is sensitive to detecting cognitive impairments including Alzheimer's disease. Measures of tau concentration in oral breath of a patient were compared to a patient's score on the two tests. Measures of tau concentration in nasal breath were also compared to a patient's score on the two tests. These comparisons were done to see whether a high tau concentration in either nasal breath, oral breath, or both, correlated to a high score on the two tests. The total Tau concentration in nasal breath was also compared to the total tau concentration in oral breath for each patient.

Sample Handling.

Samples were stored after collection and frozen to minus 80 degrees Celsius. Prior to analysis, samples were thawed completely at room temperature (requiring approximately 30 minutes) and mixed thoroughly until visibly homogenous via brief vortexing. Samples were diluted offline manually in Quanterix Tau sample diluents using the recommended 4× dilution scheme (75 micro liter sample sample into 225 micro liter sample diluent), then loaded onto the Simoa HD-1 instrument for testing.

Preparation of Tau Calibrators and Controls.

Ready-to-use reference calibrators were stored at −80° C., with values assigned against primary calibrators. Ready-to-use quality control samples were stored at −80° C. (prepared with antigen spiked into calibration buffer with established target values). Prior to analysis, calibrators and controls were brought to room temperature to thaw completely, and mixed thoroughly by brief vortexing. The control was diluted using the same dilution scheme as the samples before testing. All calibrators were assayed in triplicate; control and subject samples were tested in duplicate.

Simoa Tau Assay.

The Simoa Human Total Tau assay is a 2-step digital immunoassay to measure the quantity of total tau in a sample using the Simoa HD-1 Analyzer and Single Molecule Array (Simoa) technology. In the first step, sample, anti-tau-coated paramagnetic capture beads, and biotinylated detector antibodies are combined. Tau molecules present in the sample are captured by the anti-tau-coated capture beads and labeled with biotinylated detector antibodies. After washing, a conjugate of streptavidin-β-galactosidase (SβG) is mixed with the capture beads. SβG binds to the biotinylated detector antibodies, resulting in enzyme labeling of captured tau. Following a second wash, the capture beads are resuspended in a resorufin β-D-galactopyranoside (RGP) substrate solution and transferred to the Simoa Disc. Individual capture beads are then sealed within microwells in the array. If tau has been captured and labeled, the βgalactosidase hydrolyzes the RGP substrate into a fluorescent product that provides the signal for measurement. A single labeled tau molecule results in sufficient fluorescent signal in 30 seconds to be detected and counted by the Simoa optical system. At low tau concentration, the percentage of bead-containing wells in the array that have a positive signal is proportional to the amount of tau present in the sample. At higher tau concentration, when most of the bead-containing wells have one or more labeled tau molecules, the total fluorescence signal is proportional to the amount of tau present in the sample. The concentration of tau in unknown samples is interpolated from a standard curve.

Calibration and Control.

The Tau assay was calibrated using a 4 Parameter Logistic Curve fit data reduction method (4PLC, 1/y2 weighted) to generate a calibration curve. The limit of detection (LOD) was set as the Tau level at an AEB equal to the average of the zero calibrator+2.5 standard deviations. One control was tested with the Tau assay to verify the validity of the run. Two controls were tested with the experiment to verify the validity of the run.

Sample Analysis of Data.

All samples were run in duplicate at a 4-fold dilution unless otherwise noted.

Figure 3:
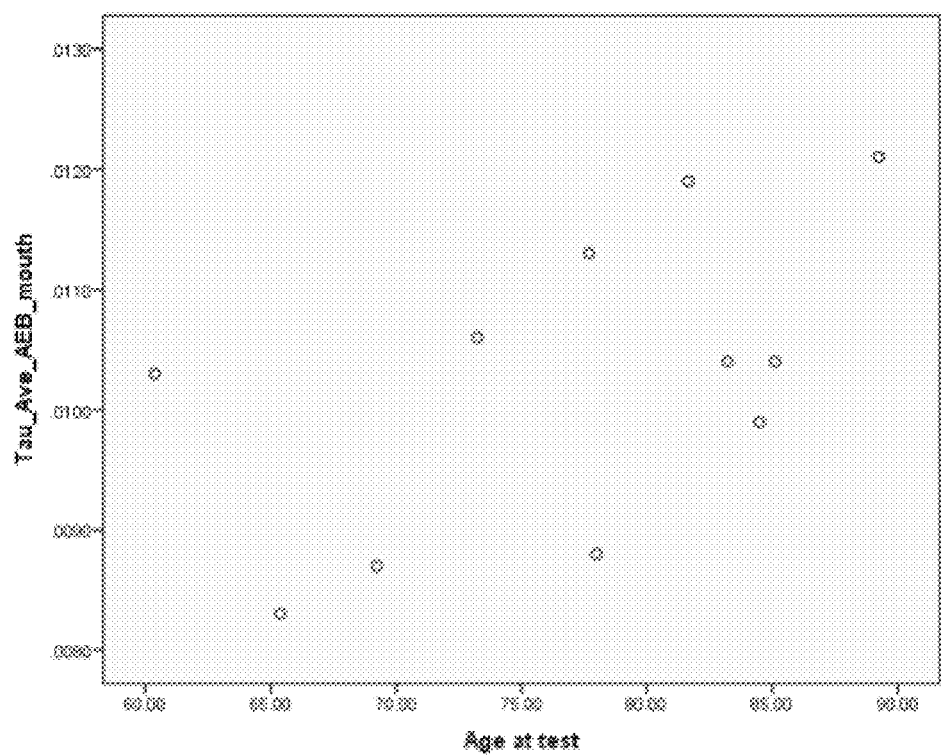
FIG. 3 is a data plot showing the tau concentration in mouth breath of certain study subjects of different ages.
Figure 4A:
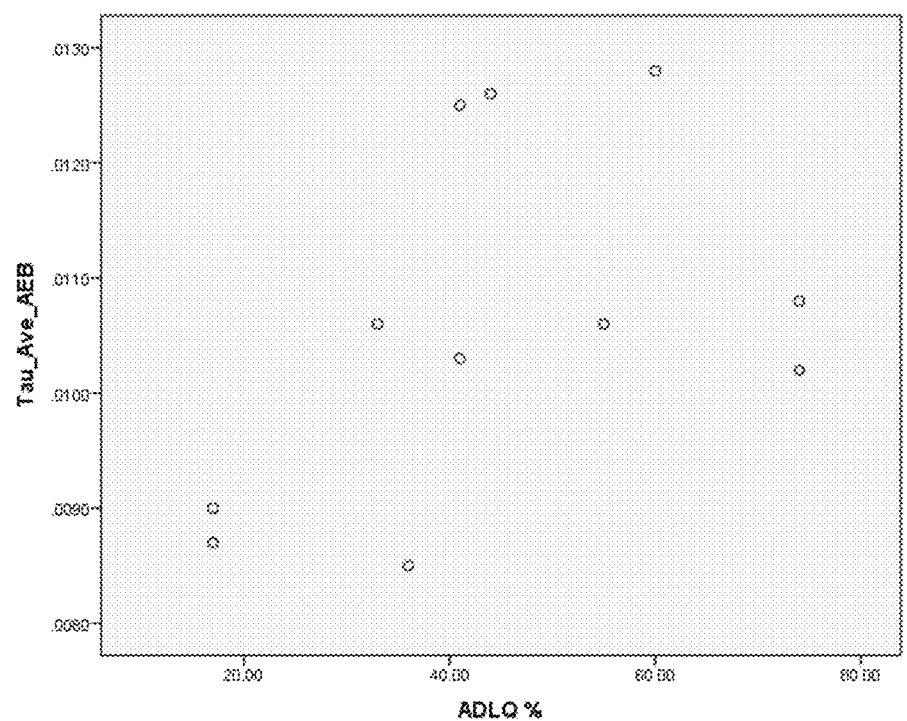
FIG. 4A is a data plot showing the tau concentrations in nose breath of certain study subjects compared to each subject's test results on the ADLQ.
Figure 4B:
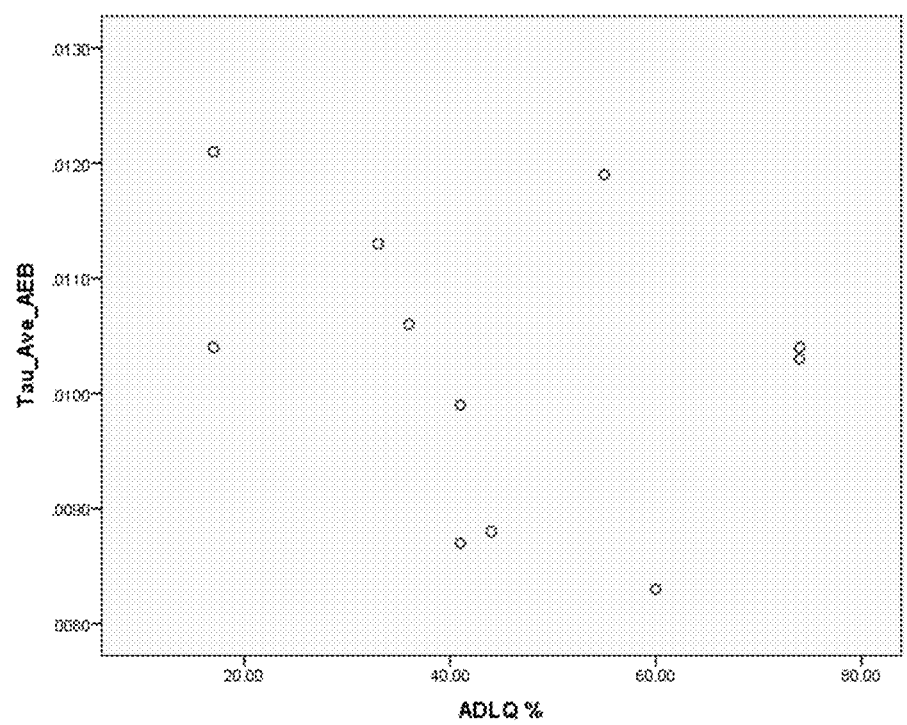
FIG. 4B is a data plot showing the tau concentrations in mouth breath of certain study subjects compared to each subject's test results on the ADLQ.
Figure 5A:
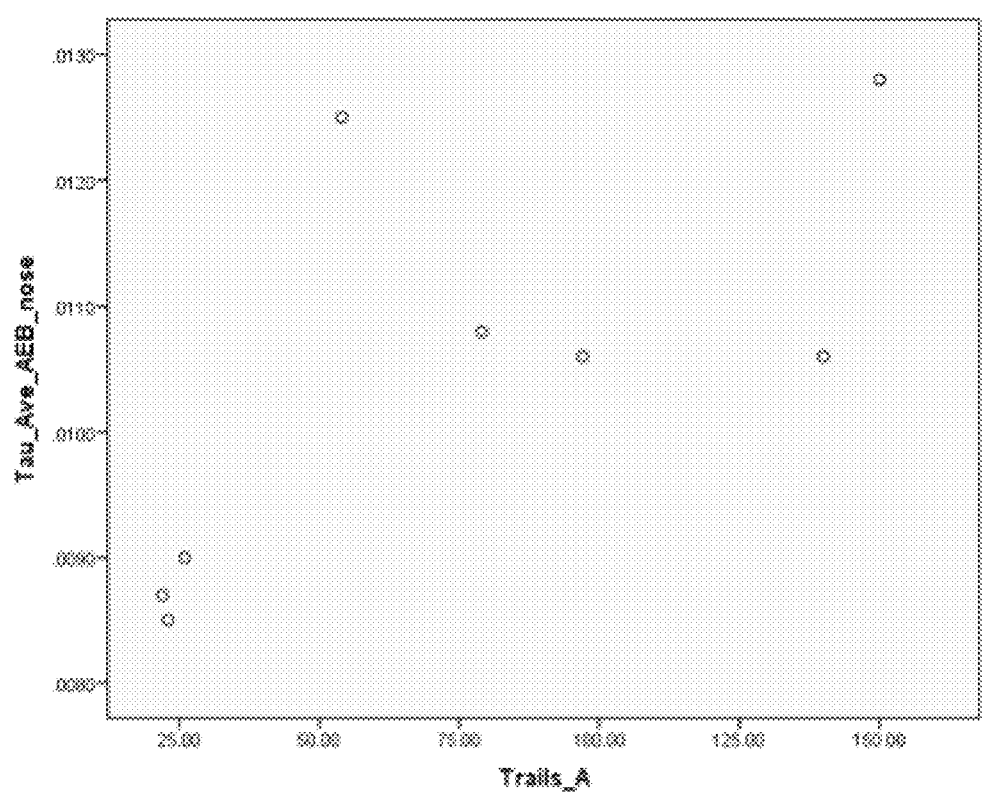
FIG. 5A is a data plot showing the tau concentrations in nose breath of certain study subjects compared to each subject's test results on the Trail Making Test.
Figure 5B:
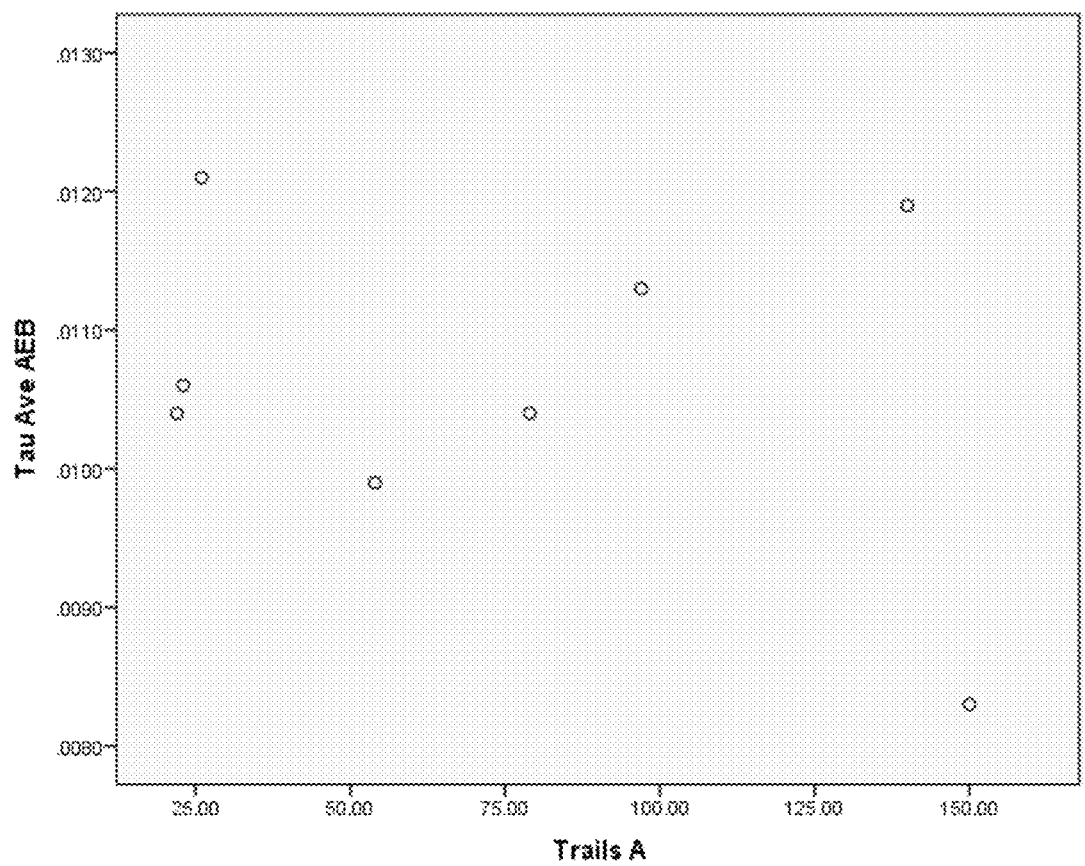
FIG. 5B is a data plot showing the tau concentrations in mouth breath of certain study subjects compared to each subject's test results on the Trail Making Test.

The results of the study indicated that tau concentration in nasal breath differs from tau concentration in mouth breath. Tau concentration was generally higher from nasal compared to oral breath across patients. Additionally, Tau concentration in mouth breath is correlated to a study subject's age, but was not correlated to a study subject's score on the ADLQ. FIG. 3 is a data plot showing the correlation, with the tau concentration in mouth breath of study subjects plotted against their ages. By contrast, tau concentration in nasal breath was found to be correlated with the study subject's score on the ADLQ. FIG. 4A is a plot that shows the correlation of tau concentration from nose breath with each study subject's score on the ADLQ while FIG. 4B is a plot that shows the correlation of tau concentration from mouth breath with study subject scores on the ADLQ. FIG. 5A is a plot that shows the correlation of tau concentration from nose breath with each study subject's score on the Trails Making Test while FIG. 5B is a plot that shows the correlation of tau concentration from mouth breath with study subject scores on the Trails Making Test. One observation revealed by FIG. 5A is that the three subjects able to complete the trails test in about 25 seconds have tau concentration from nasal breath of about 0.0090 pg/mL or lower, while the other subjects (who took 50 seconds or more) to complete the test have higher tau concentrations of nasal breath of above 0.0100 pg/mL. Based on this observation, it may be the case that tau concentration levels above 0.0100 pg/mL indicate more severe AD while tau concentration levels below 0.0100 pg/mL indicate less severe AD.

In the study, a sample of study subjects with Alzheimer's disease revealed a relationship between exhaled breath from the nose and scores on the ADLQ with a greater Tau burden associated with more impaired day-to-day functioning. No relationship was found in the study subject sample between exhaled breath from the mouth and scores on the ADLQ.

What is claimed is:

1. A method, comprising:
    collecting a nasal sample of exhaled breath from a person's nose using a nasal breath collection device;
    analyzing the nasal sample of exhaled breath from the person's nose to detect and measure a concentration of the at least one neural biomarker in the nasal sample of exhaled breath from the person's nose;
    collecting a mouth sample of exhaled breath from a person's mouth using a collection device;
    analyzing the mouth sample to detect a concentration of the at least one biomarker in the mouth sample; and
    subtracting the concentration of the at least one biomarker in the mouth sample of exhaled breath from the person's mouth from the concentration of the at least one biomarker in the nasal sample of exhaled breath from the person's nose to determine an adjusted biomarker concentration.

2. The method of claim 1, further comprising correlating the adjusted biomarker concentration with at least one medical condition.

3. The method of claim 1, further comprising condensing the nasal sample of exhaled breath from the person's nose and detecting and measuring the concentration of the at least one neural biomarker in the condensed sample of exhaled nasal breath from the person's nose.

4. The method of claim 1, further comprising vaporizing the nasal sample of exhaled breath from the person's nose and detecting and measuring the concentration of the at least one neural biomarker in the vaporized sample of exhaled nasal breath from the person's nose.

5. The method of claim 2, wherein the at least one medical condition is dementia.

6. The method of claim 2, wherein the at least one medical condition is Alzheimer's disease.

7. A method of diagnosing or assessing risk of a tauopathy in a person comprising:
    collecting a nasal sample of exhaled breath from the person's nose using a nasal breath collection device;
    analyzing the nasal sample to detect a presence and measure a concentration of tau protein in the nasal sample of exhaled breath from the person's nose;
    collecting a mouth sample of exhaled breath from a person's mouth using a collection device;
    analyzing the mouth sample to detect a presence and a concentration of tau protein in the mouth sample of exhaled breath from a person's mouth;
    determining a difference between the concentration of tau protein in the nasal sample of exhaled breath from the person's nose and the concentration of tau protein in the mouth sample of exhaled breath from the person's mouth,
    wherein the difference indicates susceptibility to Alzheimer's disease or dementia.

8. The method of claim 7, wherein the nasal sample and mouth sample are analyzed using an ELISA assay.

9. The method of claim 7, wherein the nasal sample and mouth sample are analyzed using a Simoa Human Total Tau assay.

10. The method of claim 7, wherein the nasal sample and the mouth sample are analyzed using a gas-chromatographic technique.

11. The method of claim 10, wherein the gas-chromatographic technique is combined with mass spectrometry.

* * * * *